United States Patent [19]

Berthelsen

[11] Patent Number: 4,953,564
[45] Date of Patent: Sep. 4, 1990

[54] SCREW-IN DRUG ELUTING LEAD

[75] Inventor: Wendy A.W. Berthelsen, Range, Mich.

[73] Assignee: Medtronic, Inc., Minneapolis, Minn.

[21] Appl. No.: 398,199

[22] Filed: Aug. 23, 1989

[51] Int. Cl.$^5$ ............................................. A61N 1/05
[52] U.S. Cl. .................................. 128/784; 128/642; 128/419 P
[58] Field of Search ............... 128/642, 783, 784, 785, 128/786, 802, 419 P

[56] References Cited

U.S. PATENT DOCUMENTS

| H356 | 11/1987 | Stokes et al. | 128/785 |
|---|---|---|---|
| 4,106,512 | 8/1978 | Bisping | 128/418 |
| 4,209,019 | 6/1980 | Dutcher et al. | 128/784 |
| 4,217,913 | 8/1980 | Dutcher | 128/785 |
| 4,506,680 | 3/1985 | Stokes | 128/786 |
| 4,577,642 | 3/1986 | Stokes | 128/784 |
| 4,606,118 | 8/1986 | Cannon et al. | 29/825 |
| 4,624,266 | 11/1986 | Kane | 128/419 P |
| 4,711,251 | 12/1987 | Stokes | 128/784 |
| 4,819,661 | 4/1989 | Heil, Jr. et al. | 128/786 |

Primary Examiner—Lee S. Cohen
Assistant Examiner—S. Getzow
Attorney, Agent, or Firm—Reed A. Duthler; Joseph F. Breimayer

[57] ABSTRACT

A cardiac pacing lead or other stimulation lead carrying a drug incorporated into a controlled release device. The lead is provided with an extendable fixation helix which is advanceable from the distal end of the lead in order to engage with the tissue to be stimulated and to maintain the distal end of the lead adjacent the tissue to be stimulated. The controlled release device is located within the fixation helix and is extended with the fixation helix when it is advanced out of the distal end of the lead. In its advanced position, the controlled release device is positioned adjacent the distal end of the lead, preferably in a position to contact the tissue to be stimulated.

9 Claims, 1 Drawing Sheet

SCREW-IN DRUG ELUTING LEAD

BACKGROUND OF THE INVENTION

The present invention relates generally to electrical medical leads, and more particularly to stimulation leads of the type which dispense a steroid or other drug adjacent the stimulation site. The invention is particularly useful in the context of a cardiac pacing lead.

Delivery of a drug at the stimulation site of an implantable pacing lead is disclosed in U.S. Pat. No. 4,711,251, issued to Stokes. A particularly desirable configuration for such a lead is disclosed in U.S. Pat. No. 4,506,680, also issued to Stokes. In this configuration, the drug to be dispensed is compounded with silicone rubber based medical adhesive and located within a chamber within the distal end of the stimulation electrode. The drug, a steroid, acts as an anti-inflammatory agent, reducing the adverse reaction of the tissue to the stimulation electrode.

Alternative embodiments of stimulation electrodes which elute a steroid or other drugs are disclosed in U.S. Pat. No. 4,606,118 issued to Cannon et al and in U.S. Pat. No. 4,577,642 issued to Stokes. A myocardial pacing lead adapted to deliver steroid at the stimulation site is disclosed in Statutory Invention Registration No. H356, by Stokes et al, in which a steroid is delivered through a tubular electrode to a delivery point within the myocardium.

Pacing leads with extendable fixation helixes are well known to the art, such as that disclosed in U.S. Pat. No. 4,106,512, issued to Bisping and U.S. Pat. No. 4,217,913, issued to Dutcher. In Bisping, the fixation helix functions as the stimulation electrode. In Dutcher, the fixation helix serves only to affix the end of the lead to the tissue, and the lead is provided with a separate electrode located on its distal surface. In either case, the fixation helix functions to hold the distal end of the lead against the tissue to be stimulated.

SUMMARY OF THE INVENTION

The present invention provides an electrical stimulation lead which includes an extendable active fixation device and provides the benefits associated with delivery of a glucocorticosteroid, anti-inflammatory agent, or other drug adjacent the stimulation site. This is particularly important in the context of a lead employing a barb, hook, or helix, as insertion of the active fixation device into the tissue acts as an irritant which may lead to the formation of fibrotic tissue which can interfere with the delivery of the stimulation pulse.

In the present invention, a controlled release device is incorporated in and integrated with the fixation helix such that as the helix is extended, the controlled release device is also extended. The lead is so configured that at the limit of the advancement of the fixation helix, the controlled release device is positioned at the distal end of the lead. This allows for incorporation of a controlled release device within the lead without interfering with the functioning of the extendable helix. Moreover, the steroid or other drug from the controlled release device can be limited to the immediate vicinity of the distal end of the lead, rather than allowing the drug to be dispersed into the blood stream.

In its preferred embodiment, the controlled release device is located within a housing provided with a porous elution path. If fabricated from a conductive material, the housing may also function as an electrode.

DETAILED DESCRIPTION OF THE INVENTION

Figure 1:
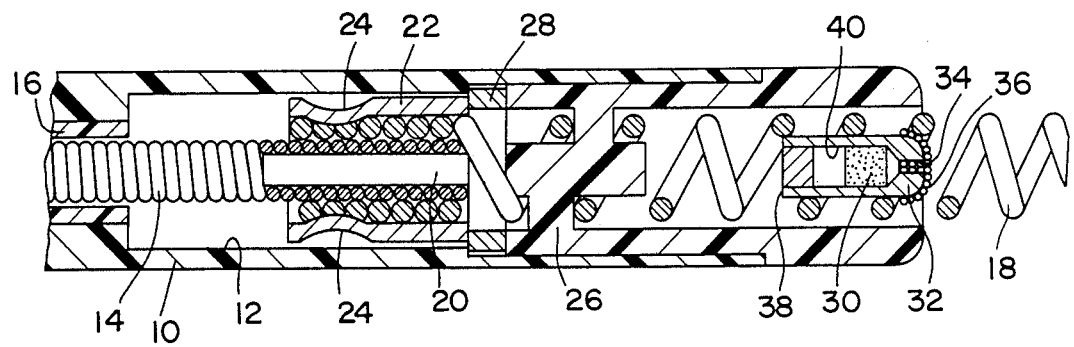
FIG. 1 is a side cutaway view of the distal end of a lead according to the present invention.

FIG. 1 is a side, cutaway view of the distal end of a cardiac pacing lead according to the present invention. The structure of the lead proximal to the portion shown may correspond to that illustrated in the article "The Impact of Pending Technologies on a Universal Connector Standard", by Doring and Flink, published in PACE, Nov.-Dec. 1986, Part 2, pp. 1186-1190, incorporated herein by reference in its entirety. Additional appropriate configurations for the proximal portion of the pacing lead are disclosed in U.S. Pat. application No. 304,756, for a "MEDICAL ELECTRICAL LEAD CONNECTOR", by Ufford et al, filed Jan. 31, 1989, also incorporated herein by reference in its entirety. Alternatively, any other conventional pacing lead construction may be used, provided that it allows for a freely rotatable member extending through the lead body and engageable with the helix.

The distal end of the pacing lead illustrated in FIG. 1 carries a molded plastic electrode head 10, which includes an internal cylindrical lumen 12. Entering the lumen 12 from the proximal end is an elongated coiled conductor 14, which may be either a monofilar or a multifilar coil. Surrounding coil 14 is a tubular insulative sheath 16, which extends to the proximal end of the lead. Coil 14 is mounted so that it rotates freely within sheath 16. Exiting the distal end of the lead is a helix 18, which is screwed into the tissue to be stimulated and functions as an electrode. Helix 18 and coil 14 are mechanically and electrically maintained in contact with one another by means of crimps 24 which mechanically compress the proximal end of helix 18 and the distal end of coil 14 between crimping core 20 and crimping sleeve 22.

As coiled conductor 14 is rotated in a clockwise direction as viewed from the distal end of the lead, helix 18 is screwed out of the distal end of electrode head 10 rotating around electrode guide 26. A radiopaque indicator ring 28 is located within lumen 12 of electrode head 10, and serves to indicate the position of helix 18. By using a fluoroscope, the physician can determine the distance between crimping sleeve 20 and indicator ring 28, and thereby determine the distance helix 18 has been screwed out of the electrode head 10.

A monolithic controlled release device 30 is located within a housing 32 which is mounted within helix 18. The drug within MCRD 30 elutes out of housing 32 by means of a porous, sintered elution path 34. Housing 32 is also provided with a porous coating 36 on its distal surface adjacent elution bore 34. At its proximal end, housing 30 is sealed by means of an end cap 38. In the embodiment illustrated, MCRD 30 takes the form of a steroid, sodium dexamethasone phosphate compounded in silicone rubber based medical adhesive. Because MCRD 30 swells in use, an expansion space 40 is provided proximal to MCRD 30. In general, MCRD 30 and housing 32 function in the same manner as the corresponding structures disclosed in U.S. Pat. No. 4,506,680, issued to Stokes, incorporated herein by reference in its entirety.

In its retracted position, the distal tip of helix 18 is located within electrode guide 26, or extends only slightly therefrom. In use, the distal end of the lead is placed adjacent the tissue to be stimulated and conductor 14 is rotated, screwing helix 18 out of the distal end of the lead and into the tissue to be stimulated. As illustrated, it is desirable that housing 32 be located such that at the maximum extension of helix 18, housing 32 is roughly adjacent the distal end of the lead. This allows the drug to be delivered directly to the tissue being stimulated. Because the distal end of electrode guide 26 is positioned adjacent the tissue to be stimulated, it helps to restrict elution of the steroid to the immediate vicinity of the distal end of the lead.

Figure 2:
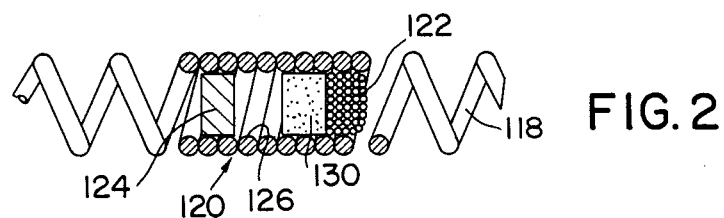
FIG. 2 is a side, cutaway view of an alternate embodiment of a fixation helix with a controlled release device for incorporation into a lead as illustrated in FIG. 1.

FIG. 2 shows an alternate embodiment of a fixation helix carrying a monolithic controlled release device. In this embodiment, the helix 118 includes a segment of close wound coil 120, which serves as the housing for the monolithic controlled release device 130. Adjacent close wound coils may be welded to one another, if desired. Located at the distal end of the close wound coil segment 120 of helix 118 is a porous, sintered plug 122, which functions as an elution path for the steroid within MCRD 30 and allows for elution of the steroid to the tissue being stimulated. At the proximal end of the close wound coil segment 120 is a plug 124 which retains steroid 130 within the helix 118. As in FIG. 1, above, an expansion space 126 is provided into which MCRD 130 may expand as it imbibes body fluid in use. As illustrated in FIG. 1, it is desirable that the distal end of the porous cap 122 should be approximately even with the distal end of electrode guide 26 when fixation helix 118 is fully extended.

Figure 3:
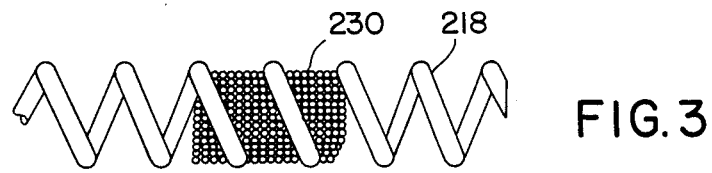
FIG. 3 is a side, plan view of a second alternate embodiment of a fixation helix with a porous drug elution matrix for incorporation in the lead of FIG. 1.

FIG. 3 shows a second alternative embodiment of a fixation helix and drug elution device. In this case, fixation helix 218 carries a porous plug 230, which has been soaked in or otherwise impregnated with the drug to be delivered. As in the case of FIG. 1, the distal end of plug 230 should be roughly adjacent the distal end of the lead when fixation helix 218 is fully extended.

In all of the above drawings, porous structures are used in conjunction with the drug elution function. These structures may be made by any one of a number of known, commercially available sintering techniques which fall into the general category of powder metallurgy. Alternatively, ceramic, plastic or other non-metallic porous structures may be used to serve as elution bores and/or drug retention mechanisms.

In the embodiment illustrated in FIG. 1, it is anticipated that electrode guide 26 will be fabricated of a non-conductive material, such as a biocompatible plastic and that helix 18 and housing 32 would be fabricated of a conductive biocompatible metal, such as platinum, titanium or MP35N alloy. In such case, the porous surface of housing 32 would serve as an electrode in conjunction with helix 18. However, helix 18 may also be provided with an insulative coating, allowing the porous surface 36 of housing 32 to function as the sole electrode.

As illustrated, the lead takes the form of a unipolar lead. However, alternative embodiments in which the lead carries additional electrodes are believed to be within the scope of the invention. For example, the ring electrode may be positioned on housing 10, as illustrated in the above-cited article by Doring and Flink, to provide a bipolar stimulation and sensing lead. Additional alternative embodiments in which the guide 26 is conductive and serves as an electrode, and in which one or both of helix 18 and housing 32 are non-conductive are also believed to be within the scope of the invention. As such, the disclosure herein should be considered exemplary, rather than limiting with regard to the following claims. In conjunction with the above specification,

I claim:

1. An electrical medical lead comprising:
   an elongated insulative lead body having a proximal end and a distal end;
   an elongated conductor, mounted within said lead body, said conductor having a proximal end and a distal end;
   an electrode assembly mounted at the distal end of said insulative lead body, said electrode assembly comprising an electrode head member having a lumen open to the distal end of said lead body; a fixation helix mounted within said lumen of said head member, said fixation helix having a proximal end and a distal end, said fixation helix mounted in said lumen of said head member such that said helix is advanceable from a first, retracted position within said lumen of said head member in which the distal end of said helix is adjacent the distal end of said lead body to a second, advanced position in which the distal end of said fixation helix projects distally of the distal end of said lead body, said electrode assembly further comprising a drug release device having a proximal end and distal end and having means for releasing a drug contained within said drug release device at least adjacent the distal end of said drug release device, said drug release device mounted to said fixation helix such that when said fixation helix is in said first, retracted position within aid lumen of said head member, the distal end of said drug release device is located within the lumen of said electrode head member and such that when said helix is advanced to said second, extended position, the distal end of said drug release device is adjacent the distal end of said lead body, the distal end of said helix extending distally of the distal end of said drug release device, said electrode assembly further comprising at least one conductive electrode surface coupled to the distal end of said elongated conductor; and
   means for advancing said fixation helix from said first, retracted position to said second, extended position.

2. A lead according to claim 1 wherein said electrode surface comprises the distal end of said drug release device.

3. A lead according to claim 1 or claim 2 wherein said electrode surface comprises said fixation helix.

4. A lead according to claim 3 wherein said fixation helix is advanced from said first, retracted position to said second, extended position by rotation of said helix, and wherein said means for advancing said helix comprises said elongated conductor, said elongated conductor being rotatably mounted within said electrode head member.

5. A lead according to claim 1 wherein said drug release device comprises a conductive housing having an elution path for said drug, located at a distal end of said housing.

6. A lead according to claim 5 wherein said housing comprises a plurality of closely spaced coils of said fixation helix.

7. A lead according to claim 5 or claim 6 wherein said elution path comprises a porous, sintered metallic structure, sintered to said housing of said drug release device.

8. A lead according to claim 1 wherein said drug release device comprises a porous member impregnated with said drug.

9. A lead according to claim 8 wherein said porous member comprises a porous, sintered metal structure, and wherein said porous sintered metal structure is sintered to said fixation helix.

* * * * *